United States Patent [19]

Howell

[11] Patent Number: 4,835,323

[45] Date of Patent: May 30, 1989

[54] HYDROQUINONES

[75] Inventor: Frederick H. Howell, Atherton, England

[73] Assignee: Ciba-Geigy AG, Basel, Switzerland

[21] Appl. No.: 906,111

[22] Filed: Sep. 11, 1986

Related U.S. Application Data

[60] Continuation-in-part of Ser. No. 628,073, Jul. 5, 1984, abandoned, Division of Ser. No. 389,992, Jun. 18, 1982, Pat. No. 4,484,000.

[30] Foreign Application Priority Data

Jun. 19, 1981 [GB] United Kingdom ............... 8119015

[51] Int. Cl.$^4$ .................... C07C 43/164; C07C 50/04; C07C 69/76

[52] U.S. Cl. ................. 568/662; 260/396 R; 260/396 K; 558/214; 560/75; 568/766

[58] Field of Search ............... 560/75; 558/214; 568/662, 766; 260/396 R, 396 K

[56] References Cited

U.S. PATENT DOCUMENTS

| | | | |
|---|---|---|---|
| 3,957,836 | 5/1976 | Morimoto et al. | 562/478 |
| 4,139,545 | 2/1979 | Morimoto et al. | 560/75 X |
| 4,271,083 | 6/1981 | Morimoto et al. | 260/396 R |

Primary Examiner—Warren B. Lone
Assistant Examiner—Vera C. Clarke

Attorney, Agent, or Firm—Wenderoth, Lind & Ponack

[57] ABSTRACT

New hydroquinones have the formula:

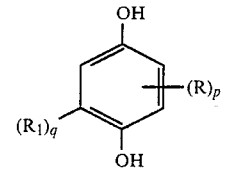

wherein p is 1 or 2 and q is 0 or 1, provided that p+q is 1 or 2;

R is a residue of formula:

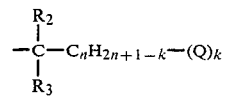

wherein Q is (i) -OX or (ii) -PO(OR$_{11}$)((O)$_x$R$_{11}$); and salts thereof with organic or inorganic acid bases.

The groups X and R$_{11}$ and x are defined hereinafter.

The compounds of formula I are useful as stabilizers in photographic materials.

8 Claims, No Drawings

HYDROQUINONES

This is a continuation-in-part of application Ser. No. 628073, filed July 5th, 1984 (now abandoned), which application is a division of application Ser. No. 389,992, filed June 18, 1982 (now U.S. Pat. No. 4,484,000).

The present invention relates to new hydroquinones and a process for their preparation.

According to the present invention, there are provided novel hydroquinones having the formula:

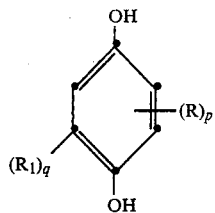

where p is 1 or 2 and q is 0 or 1, provided that p+q is 1 or 2; R is a residue of formula

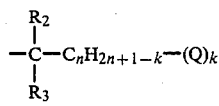

wherein Q is selected from the residues:

(i) —COZR$_4$ wherein Z is O or NR$_5$, and R$_4$ independently is H, a straight or branched chain alkyl having from 1 to 20 carbon atoms, optionally interrupted by 1 to five oxygen atoms, and optionally substituted by a group OR$_6$ wherein R$_6$ is C$_1$-C$_{12}$ alkyl, C$_3$-C$_{12}$ cycloalkyl, straight or branch C$_3$-C$_{20}$ alkenyl, C$_6$-C$_{10}$ aryl optionally substituted by one or two C$_1$-C$_4$ alkyl groups of C$_7$-C$_{13}$ aralkyl, or R$_4$ a straight or branched chain alkenyl group having from 3 to 20 carbon atoms or a cycloalkyl group having from 3 to 12 carbon atoms; an aryl group having from 6 to 10 carbon atoms optionally substituted by a C$_1$-C$_4$ alkyl group; or an aralkyl group having from 7 to 13 carbons atoms; a 5 or 6 membered heterocycle containing an oxygen atom, and optionally substituted by one or two C$_1$-C$_4$ straight- or branch chain alkyl groups; or methyl substituted by a 5 or 6 membered heterocycle containing a oxygen atom and optionally substituted by one or two C$_1$-C$_4$ straight- or branch chain alkyl groups; and when Z is —NR$_5$, R$_5$ is hydrogen or a straight or branched chain alkyl group having from 1 to 20 carbon atoms, or R$_4$ and R$_5$ together with the nitrogen atom to which they are each bonded may form a 5 or 6 membered heterocyclic ring, optionally substituted by one or two C$_1$-C$_4$ alkyl groups;

(ii) —OX wherein X is R$_5$ or —COR$_7$, wherein R$_5$ has its previous significance, R$_7$ is H or a straight- or branch chain alkyl group having from 1 to 20 carbon atoms, a straight- or branch chain alkenyl having from 3 to 20 carbon atoms, a C$_3$-C$_{12}$ cycloalkyl group, a C$_7$-C$_{13}$ aralkyl group, or a C$_6$-C$_{10}$ aryl group, optionally substituted by one or two C$_1$-C$_4$ alkyl groups;

(iii) —NR$_8$R$_9$ wherein R$_8$ is H or a straight- or branched chain alkyl group having from 1 to 12 carbon atoms and R$_9$ is H, a straight- or branched chain alkyl group having 1 to 12 carbon atoms, or an acyl group of formula —COR$_7$ wherein R$_7$ has its previous significance, or R$_8$ and R$_9$, together with the nitrogen atom to which they are each bonded, form a 5- or 6-membered ring, optionally substituted by one or two C$_1$-C$_4$ alkyl groups;

(iv) —PO(OR$_{10}$)([O])$_x$R$_{11}$) wherein x is 0 or 1, and when x is 1 R$_{10}$ and R$_{11}$ are the same or different and each is H or a straight or branched chain alkyl group having from 1 to 20 carbon atoms: or R$_{10}$ and R$_{11}$ may be linked together to form a C$_2$-C$_3$ alkylene chain optionally substituted by one or more C$_1$-C$_{20}$ alkyl groups; and when x is 0, R$_{10}$ is hydrogen or a straight- or branched chain alkyl group having from 1 to 20 carbon atoms and R$_{11}$ is a C$_1$-C$_5$ straight chain alkyl group;

(v) —SO$_2$R$_{12}$ wherein R$_{12}$ is OH, Cl or —NR$_5$R$_7$ wherein R$_5$ and R$_7$ have their previous significance; provided that, when R$_{12}$ is OH, then R$_1$ is a residue of formula II; and (vi) CN;

n is an integer from 1 to 20; k is 1 or 2; R$_2$ and R$_3$ are the same or different and each is straight or branched chain alkyl group having from 1 to 5 carbon atoms and, when Q is —CO$_2$R$_4$, either R$_2$ or R$_3$ is optionally substituted by a —CO$_2$R$_4$ group, the R$_4$ groups being independent, or R$_2$ or R$_3$ may be so linked to the residue C$_n$H$_{2n+1-k}$ that there is formed a C$_5$-C$_{12}$ cycloalkylene residue substituted by the group —(CO$_2$R$_4$)$_k$, the R$_4$ groups being independent, wherein R$_4$ and k have their previous significance; R$_1$ is C$_1$-C$_8$ straight- or branched chain alkyl, or a residue of formula II as hereinbefore defined, and when R$_1$ is a residue of formula II, then R$_1$ and R may be the same or different; and salts thereof with organic or inorganic acids and bases.

When the group R$_1$ is a C$_1$-C$_8$ straight- or branched chain alkyl group it may be, for example, a methyl, ethyl, n-propyl, isopropyl, n-butyl, iso-butyl, t-butyl, t-amyl, or 1,1,3,3-tetramethylbutyl.

When the group R$_2$ or R$_3$ is a C$_1$-C$_5$ straight or branched chain alkyl group it may be, for example, a methyl, ethyl, n-propyl, iso-propyl, n-butyl, sec-butyl, n-pentyl or neopentyl group.

When the group R$_4$ is a C$_1$-C$_{20}$ straight or branched chain alkyl group optionally interrupted by one to 5 oxygen atoms it may be, for example, a methyl, ethyl, 2-methoxyethyl, 2-ethoxyethyl, 2-n-propoxyethyl, 2-n-butoxyethyl, n-pentyl, n-hexyl, n-heptyl, n-octyl, 2-ethylhexyl, n-nonyl, n-decyl, n-dodecyl, n-tetradecyl, n-hexadecyl, n-octadecyl, n-eicosyl, —(C$_2$H$_4$O)$_2$CH$_3$, —(C$_2$H$_4$O)$_3$CH$_3$, —(C$_2$H$_4$O)$_4$CH$_3$ or —(C$_2$H$_4$O)$_5$CH$_3$ group.

When R$_4$, R$_6$ or R$_7$ is a C$_3$-C$_{20}$ straight or branched chain alkenyl group, it may be for example, a prop-2-enyl, n-but-2-enyl, 2-methylprop-2-enyl, n-pent-2-enyl, n-hex-2-enyl, n-hexa-2,4-dienyl, n-dec-10-enyl, or n-eicos-2-enyl group.

When the group R$_4$, R$_6$ or R$^7$ is a C$_3$-C$_{12}$ cycloalkyl group, it may be, for example, a cyclopropyl, cyclobutyl, cyclopentyl, cyclohexyl, cylooctyl, cyclodecyl, adamantyl, or cyclododecyl group. When the group R$_4$, R$_6$ or R$_7$ is a C$_7$-C$_{13}$ aralkyl group it may be, for example, a benzyl, phenylethyl, benzhydryl, or naphthylmethyl group.

When the group R$_4$, R$_6$ or R$_7$ is a C$_6$-C$_{10}$ aryl group optionally substituted by one or two C$_1$-C$_4$ straight or branched chain alkyl groups, it may be, a phenyl, tolyl, xylyl, cumyl, butylphenyl or naphthyl group.

When the group R$_4$ is a 5- or 6-membered heterocycle containing oxygen, and optionally substituted by one or two straight- or branch chain C$_1$-C$_4$ alkyl groups, it may be, for example, tetrahydrofuran-3-yl, tetrahydropyran-4-yl or 2,6-dimethyl-tetrahydropyran-4-yl. When the group $R_4$ is methyl substituted by a 5- or 6-membered heterocycle containing an oxygen atom, and optionally substituted by one or two straight- or branch chain $C_1$-$C_4$ alkyl groups, it may be, for example, furfuryl, tetrahydrofurfuryl or tetrahydropyran-2-yl-methyl.

When the group $R_8$ and $R_9$ is a $C_1$-$C_{12}$ straight or branched chain alkyl group it may be for example, a methyl, ethyl, n-propyl, isopropyl, n-butyl, sec-butyl group, t-amyl, 1,1,3,3-tetramethylbutyl, n-hexyl, n-nonyl, n-decyl or n-dodecyl.

When the groups $R_4$ and $R_5$, and the groups $R_8$ and $R_9$, together with the nitrogen atom to which they are bonded form a 5- or 6-membered heterocyclic ring, optionally substituted by one or two $C_1$-$C_4$ alkyl groups, this ring may be a pyrrolidine, piperidine, morpholine or a 2,5-dimethyl morpholine ring.

When the groups $R_5$, $R_7$, $R_{10}$ or $R_{11}$ are $C_1$-$C_{20}$ straight or branched chain alkyl they may be the same or different and may be methyl, ethyl, n-propyl, iso-propyl, n-butyl, sec-butyl, n-pentyl, n-hexyl, n-heptyl, n-octyl, 2-ethylhexyl, n-nonyl, n-decyl, n-dodecyl, n-tetradecyl, n-hexadecyl, n-octadecyl, or n-eicosyl groups.

When the groups $R_{10}$ and $R_{11}$ are linked to form a $C_2$ or $C_3$ methylene chain optionally substituted by one or more $C_1$-$C_{20}$ alkyl chain, they may be for example —$CH_2CH_2$—, —$CH_2$—$CH_2$—$CH_2$—, —$CH_2CH(CH_3)$—, —$CH_2CH(C_2H_5)$—, —$CH_2CH(C_{20}H_{41})$—, —$CH(CH_3)CH(CH_3)$—, —$CH$—$(CH_3)C(CH_3)_2$—, —$C(CH_3)_2C(CH_3)_2$—, —$CH_2CH_2$—$C(CH_3)_2$—, or $CH(CH_3)CH_2CH(CH_3)$— groups.

Examples of salts wherein Q is an acidic group —COOH include salts with alkali and alkaline earth metals and amines and, where Q is a $NR_8R_9$ group, salts with organic and inorganic acids for example, hydrochloric, sulphuric, para-toluene-sulphonic and oxalic acids.

In one preferred embodiment, the groups R and $R_1$ are bonded in the 2- and 5-positions, respectively, in the hydroquinones of formula I.

More preferred compounds of the invention are those having the formula III:

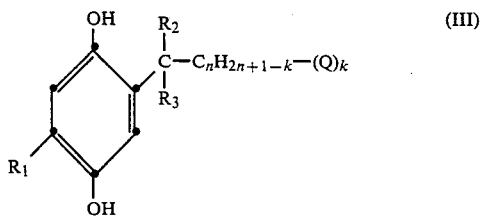

(III)

wherein $R_2$, $R_3$, n, k and Q have their previous significance and $R_1$ is a group of formula II, as hereinbefore defined, or is a group of formula IV:

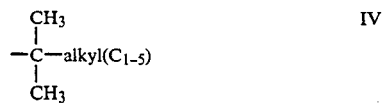

IV as well as salts thereof.

Further preferred compounds of formula III are those wherein $R_1$ is a group of formula II or IV, Q is —$COZR_4$ or —$OR_5$ wherein Z, $R_4$ and $R_5$ have their previous significance, $R_2$ and $R_3$, independently, are methyl, ethyl, n-propyl, isopropyl, or neopentyl, or either $R_2$ or $R_3$ is optionally substituted by a group —$COOR_4$ in which $R_4$ has its previous significance, or $R_2$ or $R_3$ may be so linked to the residue $C_nH_{2n+1-k}$ that there is formed a cycloalkylene residue having 5 to 8 carbon atoms which is substituted by —$COOR_4$, and n and k have their previous significance; as well as salts of these compounds.

More particularly preferred are compounds of formula III in which k is 1, $R_1$ is a group of formula II or IV, Q is —$COZR_4$ or —$OR_5$, n is an integer from 1 to 10, $R_2$ and $R_3$, independently, are methyl, ethyl or neopentyl, or one of $R_2$ and $R_3$, may be so linked to the residue $C_nH_{2n+1-k}$ that there is formed a cyclohexylene residue which is substituted by —$COOR_4$, $R_4$ is hydrogen, $C_{1-20}$-alkyl (optionally interrupted by 1, 2 or 3 oxygen atoms and/or optionally substituted by —$OR_6$ wherein $R_6$ is cyclopentyl, cyclohexyl, cyclooctyl, $C_{3-10}$ alkenyl, phenyl, benzyl, phenethyl, benzhydryl or naphthylmethyl) or $R_4$ is $C_{3-15}$ alkenyl, phenyl optionally substituted by 1 or 2 $C_{1-4}$ alkyl groups, benzyl, phenethyl, cyclopentyl, cyclohexyl or a 5- or 6-membered heterocyclic ring containing an oxygen atom, which ring is optionally substituted by 1 or 2 $C_{1-4}$-alkyl groups and $R_5$ have their previous significance, or $R_4$ and $R_5$, together with the nitrogen atom to which they are each bonded, may form a 5- or 6-membered heterocyclic ring, optionally substituted by one or two $C_{1-4}$ alkyl groups; as well as salts of these compounds.

Still further preferred compounds of formula III are those wherein k is 1, $R_1$ is a group of formula II or IV, Q is —$COZR_4$ or —$OR_4$, Z has its previous significance, n is an integer from 1 to 10, $R_2$ and $R_3$, independently, are methyl, ethyl or neopentyl or one of $R_2$ and $R_3$ may be so linked to the residue —$C_nH_{2n+1-k}$ that there is formed a cyclohexylene residue which is substituted by —$COOR_4$, $R_4$ is hydrogen, $C_{1-20}$-alkyl (optionally interrupted by 1 or 2 oxygen atoms and/or optionally substituted by cyclohexyloxy, $C_{3-C_{10}}$-alkenyloxy, phenoxy or benzyloxy) or $R_4$ is $C_{3-15}$alkenyl, phenyl, benzyl, phenethyl, cyclopentyl, cyclohexyl, or 5- or 6-membered heterocyclic ring containing an oxygen atom, or methyl substituted by a 5- or 6-membered heterocyclic ring containing an oxygen atom and is, especially, $C_{1-16}$ alkyl (optionally interrupted by an oxygen atom or optionally substituted by phenoxy) or $R_4$ is tetrahydrofuran-3-yl, tetrahydrofuran-4-yl or tetrahydrofurfuryl and $R_5$ is hydrogen or $C_{1-15}$-alkyl, or $R_4$ and $R_5$, together with the nitrogen atom to which they are each bonded, may form a 5- or 6-membered heterocyclic ring optionally substituted by one or two $C_{1-4}$-alkyl groups; as well as salts thereof.

Particularly preferred are compounds of formula III wherein k is 1, $R_1$ is a group of formula II or IV, Q is —$COZR_4$ or —$OR_5$ wherein Z has its previous significance, n is an integer from 1 to 3, $R_2$ and $R_3$ are each methyl or neopentyl, $R_4$ is hydrogen, $C_{1-16}$ alkyl (optionally interrupted by an oxygen atom or optionally substituted by phenoxy) or $R_4$ is phenyl, benzyl or tetrahydrofuran-3-yl, $R_5$ is hydrogen or $C_{1-15}$ alkyl, or $R_4$ and $R_5$, together with the nitrogen atom to which they are each bonded, may form a 5- or 6-membered heterocyclic ring optionally substituted by 1 or 2 $C_{1-4}$-alkyl groups, provided that, when Q is —$OR_5$, $R_5$ is, in particular, $C_{1-8}$ alkyl; as well as salts of these compounds.

In compounds of formula I wherein O is —$OR_5$ and n is 1 to 20, the most preferred compounds are those wherein n is 2 to 20.

Non-limiting examples of compounds of Formula I include:

Methyl 3-(2',5'-dihydroxyphenyl)-3-methyl-butyrate
n-Hexyl 3-(2',5'-dihydroxyphenyl)-3-methyl-butyrate
n-Hexyl 3-(4'-t-butyl-2',5'-dihydroxyphenyl)-3-methyl-butyrate
n-Dodecyl 3-(4'-t-butyl-2',5'-dihydroxyphenyl)-3-methyl-butyrate
2',5'-Bis-(3-methoxycarbonyl-2-methylprop-2-yl)-hydroquinone
2',5'-Bis-(3-n-hexyloxycarbonyl-2-methylprop-2-yl)-hydroquinone
2',5'-Bis-(3-n-dodecyloxycarbonyl-2-methylprop-2-yl)-hydroquinone
1-(2',5'-Dihydroxyphenyl)-4-methoxycarbonyl-1-methyl-cyclohexane
1-(2',5'-Dihydroxyphenyl)-4-n-hexyloxycarbonyl-1-methyl-cyclohexane
2',5'-Bis-(4-methoxycarbonyl-1-methyl-cyclohex-1-yl)-hydroquinone
2',5'-Bis-(4-n-hexyloxycarbonyl-1-methyl-cyclohex-1-yl)-hydroquinone
2'-(5-Methoxycarbonyl-2-methyl-pent-2-yl)-hydroquinone
2'-(5-n-Hexyloxycarbonyl-2-methyl-pent-2-yl)-hydroquinone
2'-(5-n-Hexyloxycarbonyl-2-methyl-pent-2-yl)-5'-methyl-hydroquinone
2'-(5-n-Hexyloxycarbonyl-2-methyl-pent-2-yl)-6'-methyl-hydroquinone
2'-(5-Methoxycarbonyl-2-methyl-pent-2-yl)-5'-t-butyl-hydroquinone
2'-(5-n-Hexyloxycarbonyl-2-methyl-pent-2-yl)-5'-t-butyl-hydroquinone
2'-(5-n-Dodecyloxycarbonyl-2-methyl-pent-2-yl)-5'-t-butyl-hydroquinone
2'-(5-Methoxycarbonyl-2-methyl-pent-2-yl)-5'-(1,1,3,3-tetramethylbutyl)-hydroquinone
2',5'-Bis-(5-methoxycarbonyl-2-methyl-pent-2-yl)-hydroquinone
2',5'-Bis-(5-ethoxycarbonyl-2-methyl-pent-2-yl)-hydroquinone
2',5'-Bis-(5-n-propyloxycarbonyl-2-methyl-pent-2-yl)-hydroquinone
2'-(5-n-Hexyloxycarbonyl-2-methyl-pent-2-yl)-5'-(3-n-hexyloxycarbonyl-2-methyl-prop-2-yl)-hydroquinone
2'-(5-n-Hexyloxycarbonyl-2-methylpent-2-yl)-5'-(3-n-octyloxycarbonyl-2-methyl-prop-2-yl)-hydroquinone
2',5'-Bis-(5-iso-propyloxycarbonyl-2-methyl-pent-2-yl)-hydroquinone
2',5'-Bis-(5-n-butyloxycarbonyl-2-methyl-pent-2-yl)-hydroquinone
2',5'-Bis-(5-iso-butyloxycarbonyl-2-methyl-pent-2-yl)-hydroquinone
2',5'-Bis-(5-n-pentyloxycarbonyl-2-methyl-pent-2-yl)-hydroquinone
2',5'-Bis-(5-iso-pentyloxycarbonyl-2-methyl-pent-2-yl)-hydroquinone
2',5'-Bis-(5-n-hexyloxycarbonyl-2-methyl-pent-2-yl)-hydroquinone
2',5'-Bis-(5-n-heptyloxycarbonyl-2-methyl-pent-2-yl)-hydroquinone
2',5'-Bis-(5-cyclohexyloxycarbonyl-2-methyl-pent-2-yl)-hydroquinone
2',5'-Bis-(5-octyloxycarbonl-2-methyl-pent-2-yl)-hydroquinone
2',5'-Bis-[5-(2''-ethylhexyloxycarbonyl)-2-methyl-pent-2-yl]-hydroquinone
2',5'-Bis-(5-n-dodecyloxycarbonyl-2-methyl-pent-2-yl)-hydroquinone
2',5'-Bis-(5-n-hexadecyloxycarbonyl-2-methyl-pent-2-yl)-hydroquinone
2',5'-Bis-[5-(2'-methoxyethoxycarbonyl)-2-methyl-pent-2-yl)]-hydroquinone
2',5'-Bis-[5-(2''-n-butoxyethoxycarbonyl)-2-methyl-pent-2-yl)]-hydroquinone
2',5'-Bis-[5-(2''-cyclohexyloxyethoxycarbonyl)-2-methyl-pent-2-yl)]-hydroquinone
2',5'-Bis-[5-(2''-allyloxyethoxycarbonyl)-2-methyl-pent-2-yl)]-hydroquinone
2',5'-Bis-[5-(2'-benzyloxyethoxycarbonyl)-2-methyl-pent-2-yl)]-hydroquinone
2',5'-Bis-[5-(2''-phenoxyethoxycarbonyl)-2-methyl-pent-2-yl]-hydroquinone
2',5'-Bis-(5-phenoxycarbonyl-2-methyl-pent-2-yl)-hydroquinone
2',5'-Bis-(5-benzyloxycarbonyl-2-methyl-pent-2-yl)-hydroquinone
2',5'-Bis-(5-tetrahydrofurfuryloxycarbonyl-2-methyl-pent-2-yl)-hydroquinone
2',5'-Bis-(5-furfuryloxycarbonyl-2-methyl-pent-2-yl)-hydroquinone
2',5'-Bis-(5-tetrahydropyran-4-yloxycarbonyl-2-methyl-pent-2-yl)-hydroquinone
2'-(5-n-Hexyloxycarbonyl-2-methyl-pent-2-yl)-5'-(5-methoxycarbonyl-2-methyl-pent-2-yl)-hydroquinone
2',5'-Bis-(5-carboxy-2-methylpent-2-yl)-hydroquinone and its sodium salt
2',5'-Bis-(5-carbamoyl-2-methylpent-2-yl)-hydroquinone
2',5'-Bis-(5-N-n-butylcarbamoyl-2-methylpent-2-yl)-hydroquinone
2',5'-Bis-(5-N,N-dimethylcarbamoyl-2-methylpent-2-yl)-hydroquinone
2',5'-Bis-(5-N,N-di-n-butylcarbamoyl-2-methylpent-2-yl)-hydroquinone
2',5'-Bis-(5-N-eicosylcarbamoyl-2-methylpent-2-yl)-hydroquinone
2',5'-Bis-(5-N-allylcarbamoyl-2-methylpent-2-yl)-hydroquinone
2',5'-Bis-(5-N-cyclohexylcarbamoyl-2-methylpent-2-yl)-hydroquinone
2',5'-Bis-(5-N-benzylcarbamoyl-2-methylpent-2-yl)-hydroquinone
2',5'-Bis-(5-N-phenylcarbamoyl-2-methylpent-2-yl)-hydroquinone
2',5'-Bis-(5-morpholinocarbamoyl-2-methylpent-2-yl)-hydroquinone
2'-(7-Methoxycarbamoyl-2,2,4-trimethyl-hept-4-yl)-5-t-butyl-hydroquinone
Dimethyl 5-methyl-5-(2',5'-dihydroxyphenyl)-azelate
2',5'-Bis-(2,6-dimethyl-8-hydroxy-oct-2-yl)-hydroquinone
2',5'-Bis-(8-acetyloxy-2,6-dimethyl-oct-2-yl)-hydroquinone
2',5'-Bis-(2,6-dimethyl-8-propionyloxy-oct-2-yl)-hydroquinone
2',5'-Bis-(8-butyryloxy-2,6-dimethyl-oct-2-yl)-hydroquinone
2',5'-Bis-(2,6-dimethyl-8-hexanoyloxy-oct-2-yl)-hydroquinone
Diethyl-5-(4'-t-butyl-2',5'-dihydroxyphenyl)-2-ethoxycarbonyl-5-methyl-hexane-2-phosphonate
2',5'-Bis-(5,5-diethoxycarbonyl-2-methyl-pent-2-yl)-hydroquinone
2',5'-Bis-(2,6-dimethyl-8-eicosanoyloxy-oct-2-yl)-hydroquinone 2',5'-Bis-(8-crotonoyloxy-2,6-dimethyl-oct-2-yl)-hydroquinone 2',5'-Bis-(8-benzoyloxy-2,6-dimethyl-oct-2-yl)-hydroquinone 2',5'-Bis-(2,6-dimethyl-8-phenacetyloxy-oct-2-yl)-hydroquinone 2',5'-Bis-(8-cyclohexylcarbonyloxy-2,6-dimethyl-oct-2-yl)-hydroquinone 2',5'-Bis-(8-methoxy-2,6-dimethyl-oct-2-yl)-hydroquinone 2',5'-Bis-(8-n-butoxy-2,6-dimethyl-oct-2-yl)-hydroquinone 2',5'-Bis-(6-amino-2-methyl-hept-2-yl)-hydroquinone and its hydrochloride 2',5'-Bis-(6-N-methylamino-2-methyl-hept-2-yl)-hydroquinone 2',5'-Bis-(6-N,N-dimethylamino-2-methyl-hept-2-yl)-hydroquinone 2',5'-Bis-(6-N-ethylamino-2-methyl-hept-2-yl)-hydroquinone 2',5'-Bis-(6-N,N-diethylamino-2-methyl-hept-2-yl)-hydroquinone 2',5'-Bis-(6-N,N-di-n-butylamino-2-methyl-hept-2-yl)-hydroquinone 2',5'-Bis-(2-methyl-6-morpholino-hept-2-yl)-hydroquinone 2',5'-Bis-(6-acetamido-2-methyl-hept-2-yl)-hydroquinone 2'-(6-acetamido-2-methyl-hept-2-yl)-hydroquinone 2',5'-Bis-(6-hexanamido-2-methyl-hept-2-yl)-hydroquinone 2',5'-Bis-(12-Amino-2,13-dimethyl-tetradec-2-yl)-hydroquinone 2',5'-Bis-(12-amino-3,13-dimethyl-tetradec-3-yl)-hydroquinone 2',5'-Bis-(12-acetamido-2,13-dimethyl-tetradec-2-yl)-hydroquinone 2',5'-Bis-(12-acetamido-3,13-dimethyl-tetradec-3-yl)-hydroquinone 3-(2',5'-Dihydroxyphenyl)-3-methyl-butane-phosphonic acid and its sodium salt 2',5'-Bis-(2-methyl-4-phosphono-but-2-yl)-hydroquinone Dimethyl 3-(2',5'-dihydroxyphenyl)-3-methyl-butane-phosphonate Diethyl 3-(2',5'-dihydroxyphenyl)-3-methyl-butane-phosphonate Di-n-butyl-3-(2',5'-dihydroxyphenyl)-3-methyl-butane-phosphonate Dimethyl 3-(4'-t-butyl-2',5'-dihydroxyphenyl)-3-methyl-butane-phosphonate Dimethyl 2-[4'-(1,1,3,3-tetramethylbutyl)-2',5'-dihydroxyphenyl]-3-methyl-butane phosphonate 2',5'-Bis-(2-methyl-4-di-methylphosphono-but-2-yl)-hydroquinone 2',5'-Bis-(2-methyl-4-di-ethylphosphono-but-2-yl)-hydroquinone 2',5'-Bis-(2-methyl-4-di-n-propylphosphono-but-2-yl)-hydroquinone 2'-(5-n-Hexyloxycarbonyl-2-methyl-pent-2-yl)-5'-(2-methyl-4-diethylphosphono-but-2-yl)-hydroquinone 2',5'-Bis-(2-methyl-4-di-iso-propylphosphono-but-2-yl)-hydroquinone 2',5'-Bis-(2-methyl-4-di-n-butyl-phosphono-but-2-yl)-hydroquinone 2',5'-Bis-[2-methyl-4-(di-2-ethylhexylphosphono)-but-2-yl]-hydroquinone 2',5'-Bis-(2-methyl-4-di-n-dodecylphosphono-but-2-yl)-hydroquinone 2',5'-Bis-[2-methyl-4-(2-oxo-1,3,2-dioxaphospholan-2-yl]-hydroquinone 2',5'-Bis-[2-methyl-4-(4-methyl-2-oxo-1,3,2-dioxaphospholan-but-2-yl)]-hydroquinone 2',5'-Bis-[4-(ethyl-ethylphosphino)-2-methyl-but-2-yl]-hydroquinone 2',5'-Bis-(2-methyl-3-sulpho-prop-2-yl)-hydroquinone 2-(2',5'-Dihydroxyphenyl)-2-methyl-propane sulphonamide 2-(4'-t-Butyl-2',5'-dihydroxyphenyl)-2-methyl-propane sulphonamide N-Methyl-2-(2',5'-dihydroxyphenyl)-2-methyl-propane sulphonamide N-Methyl-2-[2',5'-dihydroxy-4'-(1,1,3,3-tetramethylbutyl)-phenyl]-2-methyl-propane sulphonamide N,N-Di-n-butyl-2-(2',5'-dihydroxyphenyl)-2-methyl-propane sulphonamide N,n-Octyl-2-(2',5'-dihydroxyphenyl)-2-methyl-propane sulphonamide N,n-Octyl-2-(4'-t-butyl-2',5'-dihydroxyphenyl)-2-methyl-propane sulphonamide 2',5'-Bis(5-cyano-2-methyl-pent-2-yl)-hydroquinone.

The present invention also provides a process for the production of compounds of formula I comprising reacting, in the presence of an acid catalyst, a hydroquinone having the formula:

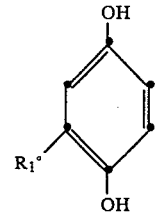

wherein R°₁ is H or a group R₁, as hereinbefore defined, with a functional alkylating agent (VI) capable of introducing a group of formula II, as hereinbefore defined.

The alkylation step is conveniently carried out at a temperature ranging from 20° C. to 150° C., but preferably in the range 80°–130° C. The acid catalyst may be a Bronsted or Lewis acid or active earth. Bronsted acids suitable for the purpose may be organic or inorganic or a partial salt thereof and may be an inorganic mineral acid such as hydrochloric, sulphuric, perchloric, and orthophosphoric acid; an alkyl, aryl or alkaryl substituted inorganic acid such as methane and ethane sulphonic acids, benzene sulphonic acid, p-toluene sulphonic acid and methane phosphonic acid; an organic acid such as dichloro acetic acid, trichloroacetic acid, and trifluoroacetic acids. Lewis acids suitable for alkylation include boron trifluoride, ferric chloride, aluminium chloride, and stannic chloride. Active earths suitable for alkylation include Fulmont®237 and Fulcat®22.

The preferred catalyst for the alkylation is p-toluene sulphonic acid. Compounds of formula I where q is 0 or 1 and p is 1 may be obtained from V where R°₁ is H or C₁–C₈ alkyl, or residue II using from 0.1 to 1.0 moles of alkylating agent VI per mole of compound of formula V.

Alternatively compounds of formula I wherein q is 1 and R₁ is C₄–C₈ may be prepared from compounds of formula I where q is 0 and p is 1 by alkylation of I with at least one mole of a $C_4$ to $C_8$ olefin or alcohol in the presence of an acid catalyst. Compounds of formula I where the two R groups II to be introduced are the same, may be obtained from V in which $R°_1$ is H using at least 2 moles of an alkylating agent VI per mole of V.

Examples of hydroquinones V include
Hydroquinone
Toluhydroquinone
2-Ethylhydroquinone
2-Propylhydroquinone
2-Isopropylhydroquinone
2-n-Butylhydroquinone
2-Isobutylhydroquinone
2-sec-Butylhydroquinone
2-t-Butylhydroquinone
2-(1,1,3,3-tetramethylbutyl)hydroquinone.

Functional alkylating agents VI which are reacted with the hydroquinone V contain a reactive centre, for example, an olefinic or hydroxy group which is eliminated, transformed or rearranged during the course of the alkylation reaction.

Examples of functional olefins suitable for the functional alkylation of compounds of formula V are:
5-Methylhex-5-enoic acid
Methyl 5-methylhex-5-enoate
Ethyl 5-methylhex-5-enoate
n-Propyl 5-methylhex-5-enoate
iso-Propyl 5-methylhex-5-enoate
n-Butyl 5-methylhex-5-enoate
iso-Butyl 5-methylhex-5-enoate
sec-Butyl 5-methylhex-5-enoate
n-Pentyl 5-methylhex-5-enoate
iso-Pentyl 5-methylhex-5-enoate
sec-Pentyl 5-methylhex-5-enoate
n-Hexyl 5-methylhex-5-enoate
Cyclohexyl 5-methylhex-5-enoate
2-Ethylhexyl 5-methylhex-5-enoate
n-octyl 5-methylhex-5-enoate
n-Dodecyl 5-methylhex-5-enoate
n-Hexadecyl 5-methylhex-5-enoate
Methyl 5,7,7-trimethyl-oct-4-enoate
1,7-Di-methoxycarbonyl-4-methyl-hept-3-ene
6-Carbomethoxy-1-methylcyclohex-1-ene
Dimethylprenylphosphonate
Diethylprenylphosphonate
Dipropylprenylphosphonate
Di-isopropylprenylphosphonate
Di-n-butylprenylphosphonate
Di-n-octylprenylphosphonate
Citronellol
Citronellyl acetate
Citronellyl methyl ether
Citronellyl butyl ether
2-Amino-6-methyl-hept-5-ene
2-Amino-6-methyl-hept-6-ene
Diethyl 2-ethoxycarbonyl-5-methyl-hex-4-ene-2-phosphonate
Ethyl 2-ethoxycarbonyl-5-methyl-hex-4-enoate.
2-Acetamido-6-methyl-hept-5-ene
2-Acetamido-6-methyl-hept-6-ene
2-Methyl-2-propene-1-sulphonic acid
2-Methyl-2-propene-1-sulphonic acid amide
N-n-Butyl-2-propene-1-sulphonic acid amide
N,N-Di-n-butyl-2-propene-sulphonic acid amide
N-n-Octyl-2-propene-1-sulphonic acid amide.

Examples of functional hydroxy compounds suitable for the functional alkylation of compounds of formula V are
2-Amino-6-hydroxy-6-methylheptane
2-Acetamido-6-hydroxy-6-methylheptane
11-Amino-2,2,12-trimethyl-tridecan-1-ol
as well as members selected from 11-amino-undecanols of the formula:

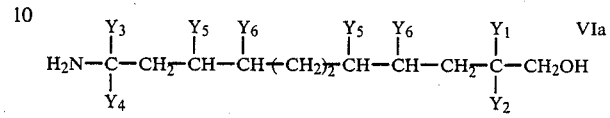

wherein $Y_1$ and $Y_3$, independently, are H or $C_1$-$C_8$ alkyl; $Y_2$ and $Y_4$, independently, are $C_1$-$C_8$ alkyl; and $Y_5$ and $Y_6$, independently, are H or $C_1$-$C_4$ alkyl.

These 11-amino-undecanols are described in more detail, together with thrie method of manufacture in German Offenlegungsschrift No. 2831299.

Examples of olefins suitable for the alkylation of compounds of formula I wherein q is 0 and p is 1 are isobutylene and diisobutylene. Examples of alcohols suitable for the alkylation of compounds of formula I wherein q is 0 and p is 1 are t-butanol and 1,1,3,3-tetramethylbutan-1-ol.

Any functional derivative of a compound of formula I may be converted to a different functional derivative. For example when Q is the acid group —$CO_2H$ it may be esterified with an alcohol $R_4$—OH to give the corresponding ester —$CO_2R_4$, or when Q is the ester group —$CO_2R_4$ it may be transesterified to give a different $R_4$ group, or alternatively the ester group —$CO_2R_4$ may be converted to an amide —$CONR_4R_5$ by treatment with $NHR_4R_5$, wherein $R_4$ and $R_5$ have their previous significance.

Suitable catalyst of the transesterification are e.g. p-toluene sulphonic acid and camphor sulphonic acid.

The present invention provides a valuable means of introducing a wide variety of functional alkyl residues into the hydroquinone molecule, in order to optimise the photographic effect of the said hydroquinone. For example, the polarity of and/or the ballast in the hydroquinones of formula I can be regulated and hence can provide an effective control of solubility, compatibility and mobility/immobility for photographic systems. Such qualities render the hydroquinones of formula I valuable intermediates for the preparation of more complex photographically useful compounds and make them useful as photographic stabilisers.

The hydroquinone compounds of the formula (1) as well as colour couplers can be incorporated in a known manner in photographic layers, for example in silver halide emulsions containing gelatine and/or other binders.

For example, they can be used in silver bromide, silver chloride or silver iodide emulsions or in those emulsions which contain a mixture of silver halides, such as silver bromide/iodide or silver chloride/bromide emulsions.

The emulsions can be chemically sensitised and they can also contain customary organic stabilisers and antifogging agents as well as customary plasticisers, for example glycerine. The emulsions can also be hardened with the hardeners customary for gelatine. Furthermore, the emulsions can contain customary coating assistants. The emulsions can be applied to layer supports customary for photographic recording material. Optionally, a mixture of several colloids can be used to disperse the silver halides.

The customary developer baths can be employed for developing the recording material for colour photography. These baths as a rule contain a developer substance of the p-phenylenediamine type, a development retarder, such as potassium bromide, an antioxidant, such as sodium sulfite, and a base, for example an alkali metal hydroxide or alkali metal carbonate. Furthermore, the developer baths can contain a conventional antifogging agent and complexing agents.

Corresponding application possibilities are described, for example, in U.S. Pat. Nos. 2.304.939, 2.304.940, 2.322.027, 2.284.879, 2.801.170, 2.801.171, 2.749.360 and 2.825.382.

The compounds of the invention also exhibit other advantages over known hydroquinones, for instance they have superior stability to actinic light, and may hence have a longer storage life.

The present invention is further illustrated by the following Examples, in which parts and percentages shown therein are by weight.

Example 1

110 Parts of hydroquinone, 284 parts of methyl-5-methyl-hex-5-enoate, and 10 parts of p-toluene sulphonic acid are heated on a steam-bath for 24 hours. The cooled reaction mixture partially solidified and after trituration with ether, yields after filtration, 2',5'-bis-(5-methoxycarbonyl-2-methylpent-2-yl)-hydroquinone, m.p. 150°–3° C. After crystallisation from methanol/water, the product has m.p. of 160°–2° C. with the following percentage composition by weight.

|  | Carbon | Hydrogen |
|---|---|---|
| Found | 67.05 | 8.96 |
| Calculated for $C_{22}H_{34}O_6$ | 66.98 | 8.69 |

Example 2

25.0 Parts of 2',5'-bis-(5-methoxycarbonyl-2-methyl-pent-2-yl)-hydroquinone, 250 parts of glacial acetic acid, and 125 parts of 46% aqueous hydrobromic acid are stored for 15 hours at room-temperature. At the end of this period, 2',5'-bis-(5-carboxy-2-methyl-pent-2-yl)-hydroquinone containing ½ molecule of acetic acid of crystallisation, is filtered off with m.p. 221°–4° C. and with the following percentage composition by weight.

|  | Carbon | Hydrogen |
|---|---|---|
| Found | 63.68 | 8.38 |
| Calculated for $C_{20}H_{30}O_6(CH_3CO_2H)_{\frac{1}{2}}$ | 63.62 | 8.14 |

5.0 Parts of 2',5'-bis-(5-carboxy-2-methylpent-2-yl)-hydroquinone, 100 parts of absolute ethanol, and 1.0 parts of 98% sulphuric acid are refluxed for 16 hours. The solution is then stripped down under reduced pressure, the residue taken up in ether, and washed with sodium bicarbonate solution. The ethereal solution after being concentrated and diluted with 40°–60° C. petroleum ether yields 2',5'-bis-(5-ethoxycarbonyl-2-methyl-pent-2-yl)-hydroquinone, m.p. 146°–9° C. with the following percentage composition by weight.

|  | Carbon | Hydrogen |
|---|---|---|
| Found | 68.62 | 9.43 |
| Calculated for $C_{24}H_{38}O_6$ | 68.22 | 9.06 |

Examples 3 to 20 in the following table further exemplify esters similarly prepared from 2',5'-bis-(5-carboxy-2-methylpent-2-yl)-hydroquinone, according to the procedure described in Example 2.

| Example | Di-ester of 2',5'-bis-(5-carboxy-2-methyl-pent-2-yl)-hydroquinone | m.p. °C. | Molecular Formula | Found and Required % Composition | |
|---|---|---|---|---|---|
|  |  |  |  | Carbon | Hydrogen |
| 3 | n-propyl | 134–6 | $C_{26}H_{42}O_6$ | 69.08 | 9.29 |
|  |  |  |  | 69.30 | 9.36 |
| 4 | iso-propyl | 140–3 | $C_{26}H_{42}O_6$ | 68.57 | 9.70 |
|  |  |  |  | 69.30 | 9.36 |
| 5 | n-butyl | 105–8 | $C_{28}H_{46}O_6$ | 70.54 | 9.97 |
|  |  |  |  | 70.26 | 9.69 |
| 6 | iso-butyl | 135–8 | $C_{28}H_{46}O_6$ | 70.57 | 9.97 |
|  |  |  |  | 70.26 | 9.96 |
| 7 | n-pentyl | 80–4 | $C_{30}H_{50}O_6$ | 71.88 | 11.10 |
|  |  |  |  | 71.11 | 9.95 |
| 8 | iso-pentyl | 94–7 | $C_{30}H_{50}O_6$ | 70.65 | 9.97 |
|  |  |  |  | 71.11 | 9.95 |
| 9 | n-hexyl | 85–7 | $C_{32}H_{54}O_6$ | 71.77 | 10.23 |
|  |  |  |  | 71.87 | 10.18 |
| 10 | cyclo-hexyl | 176–80 | $C_{32}H_{50}O_6$ | 72.61 | 9.74 |
|  |  |  |  | 72.42 | 9.50 |
| 11 | n-heptyl | 87–8 | $C_{34}H_{58}O_6$ | 72.75 | 10.48 |
|  |  |  |  | 72.56 | 10.39 |
| 12 | 2-ethylhexyl | 60–2 | $C_{36}H_{62}O_6$ | 73.15 | 10.76 |
|  |  |  |  | 73.18 | 10.58 |
| 13 | n-octyl | 77–80 | $C_{36}H_{62}O_6$ | 73.39 | 10.71 |
|  |  |  |  | 73.18 | 10.58 |
| 14 | n-dodecyl | 77–9 | $C_{44}H_{78}O_6$ | 75.46 | 10.91 |
|  |  |  |  | 75.21 | 11.11 |
| 15 | n-hexadecyl | 81–4 | $C_{52}H_{94}O_6$ | 76.48 | 11.59 |
|  |  |  |  | 76.65 | 11.54 |
| 16 | allyl | 136–9 | $C_{26}H_{38}O_6$ | 70.14 | 8.61 |
|  |  |  |  | 69.93 | 8.58 |
| 17 | tetrahydrofurfuryl | 112–4 | $C_{30}H_{46}O_8$ | 67.23 | 8.90 |
|  |  |  |  | 67.39 | 8.67 |
| 18 | 2-n-butoxyethyl | 87–9 | $C_{32}H_{54}O_8$ | 67.70 | 9.88 |
|  |  |  |  | 67.81 | 9.60 |
| 19 | 2-phenoxyethyl | 140–3 | $C_{36}H_{46}O_8$ | 70.63 | 7.98 |
|  |  |  |  | 71.26 | 7.64 |
| 20 | benzyl | 139–41 | $C_{34}H_{42}O_6$ | 74.57 | 7.89 |
|  |  |  |  | 74.70 | 7.74 |

Example 21

8.0 Parts of 2',5'-bis-(5-methoxycarbonyl-2-methyl-pent-2-yl)-hydroquinone, 100 parts of furfuryl alcohol and 1.0 parts of sodium methoxide are heated on a steam bath for 24 hours. The cooled reaction mixture is diluted with ether and washed with water. After removing the ether and excess furfuryl alcohol, the residue is triturated with 40°–60° petroleum ether containing ether to yield 2',5'-bis-(5-furfuryloxycarbonyl-2-methyl-pent-2-yl)-hydroquinone, m.p. 139°–42° C. Crystallisation from methanol containing 5% water gives crystals m.p. 140°–3° C. with the following percentage composition by weight.

|  | Carbon | Hydrogen |
|---|---|---|
| Found | 67.45 | 7.50 |
| Calculated for $C_{30}H_{38}O_8$ | 68.42 | 7.27 |

Example 22

5.5 Parts of hydroquinone, 21.2 parts of n-hexyl 5-methyl-hex-5-enoate, and 1.0 parts of p-toluene sulphonic acid are heated on a steam bath for 4 days. The cooled reaction mixture is taken up in ether, washd with 10% sodium hydroxide solution and then with water, until neutral. After stripping, the residual oil which partially solidified, is triturated with 40°–60° petroleum ether and gave 2',5'-bis-(5-n-hexyloxycarbonyl-2-methyl-pent-2-yl)-hydroquinone m.p. 77°–8° C. A further crystallisation from 60°–80° C. petroleum ether gives material m.p. 83°–6° C. identical with that obtained in Example 9.

Example 23

2.0 Parts of bis-2',5'-(5-methoxycarbonyl-2-methyl-pent-2-yl)-hydroquinone, and 15.0 parts of n-butylamine are refluxed for 18 hours and the excess butylamine then removed under reduced pressure. The residue after treatment with ether gives 2',5'-bis-(5-N-n-butylcarbamoyl-2-methyl-pent-2-yl)-hydroquinone, which after crystallisation from ethanol, has m.p. 198°–200° C. and the following percentage composition by weight.

|  | Carbon | Hydrogen | Nitrogen |
|---|---|---|---|
| Found | 70.39 | 10.21 | 5.83 |
| Calculated for $C_{28}H_{48}N_2O_4$ | 70.55 | 10.15 | 5.88 |

Example 24

2.0 Parts of bis-2',5'-(5-methoxycarbonyl-2-methyl-pent-2-yl)-hydroquinone, and 10.0 parts of di-n-butylamine are sealed into a glass Carius tube and heated at 160° C. for 72 hours. After removing the excess dibutylamine under reduced pressure, the solid residue is washed with ether and gives bis-2',5'-(5-di-N,N-n-butyl carbamoyl-2-methyl-pent-2-yl)-hydroquinone, m.p. 175°–9° C. Two further crystallisations from ethanol gives product m.p. 190°–2° C. with the following percentage composition by weight.

|  | Carbon | Hydrogen | Nitrogen |
|---|---|---|---|
| Found | 73.06 | 11.35 | 4.83 |
| Calculated for $C_{36}H_{64}N_2O_4$ | 73.42 | 10.95 | 4.76 |

Example 25

5.5 Parts of hydroquinone, 19.8 parts of citronellyl acetate and 1.0 parts of p-toluene sulphonic acid are heated on a steam-bath for 24 hours. The reaction mixture is then taken up in ether, washed with 10% sodium hydroxide solution, water, and evaporated to give a residue. This residue is distilled using a short-path distillation at 0.13 mb and gives 2',5'-bis-(8-acetoxy-2,6-dimethyl-oct-2-yl)-hydroquinone as a viscous amber oil which slowly solidified. Crystallisation from 60°–80° petroleum-ether gives product m.p. 60°–2° C. and the following percentage composition by weight.

|  | Carbon | Hydrogen |
|---|---|---|
| Found | 73.18 | 10.58 |
| Calculated for $C_{36}H_{62}O_6$ | 73.15 | 10.76 |

Example 26

5.5 Parts of hydroquinone, 15.4 parts of 1-methyl-4-methoxycarbonylcyclohex-1-ene, and 0.5 parts of p-toluene sulphonic acid are heated on a steam-bath for 3 days. The reaction mixture after dilution with ether gives a stereoisomeric mixture of 2',5'-bis-(4-methoxycarbonyl-1-methyl-cyclohex-1-yl)-hydroquinones m.p. 266°–83° C. Crystallisation from dimethylformamide and water gives product m.p. 268°–87° C. containing 1 mole of dimethylformamide of crystallisation, and the following percentage composition by weight.

|  | Carbon | Hydrogen | Nitrogen |
|---|---|---|---|
| Found | 65.65 | 8.32 | 2.28 |
| Calculated for $C_{24}H_{34}O_6 \cdot C_3H_7NO$ | 65.96 | 8.41 | 2.85 |

Example 27

12.4 Parts of toluhydroquinone, 21.2 parts of n-hexyl 5-methyl-hex-5-enoate, and 0.3 parts of p-toluene sulphonic acid are reacted and worked up as described in Example 25. Distillation under pressure gives a fraction $b_{0.1}$ 217°–26° C. which analysis showed to contain 14% of n-hexyl 5-(2',5'-dihydroxy-3'-methylphenyl)-5-methylhexanoate and 82% of n-hexyl-5-(2',5'-dihydroxy-4'-methylphenyl)-5-methyl-hexanoate and which has the following percentage composition by weight:

|  | Carbon | Hydrogen |
|---|---|---|
| Found | 71.24 | 10.11 |
| Calculated for $C_{20}H_{32}O_4$ | 71.39 | 9.59 |

Example 28

16.6 Parts of 2-t-butylhydroquinone, 14.2 parts of methyl 5-methyl-hex-5-enoate and 0.5 parts of p-toluene sulphonic acid are reacted and worked up as described for Example 25. Distillation gives methyl 5-(4'-t-butyl-2',5'-dihydroxyphenyl)-5-methylhexanoate, $b_{0.3}$ 186°–210° C. This fraction, after crystallisation from 40°–60° petroleum ether, has m.p. 136°–9° C. and the following percentage composition by weight.

|  | Carbon | Hydrogen |
|---|---|---|
| Found | 70.39 | 9.39 |
| Calculated for $C_{18}H_{28}O_4$ | 70.10 | 9.15 |

Example 29

The methyl ester of Example 28, 5.0 parts, is converted to the corresponding n-hexyl ester after reaction with 20 parts n-hexanol and 0.25 parts of sodium methoxide in a sealed glass tube for 7 days. The reaction mixture is diluted with ether, washed with dilute hydrochloric acid, then water, and stripped for ether and excess hexanol under reduced pressure to yield a residue. Short-path distillation of this residue at 0.4 mb. gives n-hexyl 5-(4'-t-butyl-2',5'-dihydroxyphenyl)-5-methyl-hexanoate as an amber oil with the following percentage composition by weight.

|  | Carbon | Hydrogen |
|---|---|---|
| Found | 72.33 | 10.26 |
| Calculated for $C_{23}H_{38}O_4$ | 72.98 | 10.12 |

Example 30

Similarly by the procedure of Example 29 from n-dodecanol and the methyl ester of Example 28, is prepared n-dodecyl 5-(4'-t-butyl-2',5'-dihydroxyphenyl)-5-hexanoate with the following percentage composition by weight.

|  | Carbon | Hydrogen |
|---|---|---|
| Found | 75.49 | 11.01 |
| Calculated for $C_{29}H_{50}O_4$ | 75.28 | 10.89 |

Example 31

83 Parts of 2-t-butylhydroquinone, 17.8 parts of dimethylprenylphosphonate, and 5.0 parts of Fulmont ® 237 are stirred at 130° C. for 24 hours. The cooled reaction mixture is diluted with ether, filtered free of catalyst, and the ether solution washed firstly with 10% sodium hydroxide solution to remove t-butyl hydroquinone and then with water.

The ethereal extract is then evaporated and the residue diluted with 40°–60° petroleum ether containing ether. After being set aside at 0° C. there is obtained a light brown solid, m.p. 153°–65° C. which following a further crystallisation from ether containing a little acetone, give dimethyl 3-(4'-t-butyl-2',5'-dihydroxyphenyl)-3-methylbutane-phosphonate with m.p. 193°–5° C. with the following percentage composition by weight.

|  | Carbon | Hydrogen | Phosphorus |
|---|---|---|---|
| Found | 59.99 | 8.38 | 8.62 |
| Calculated for $C_{17}H_{29}O_5P$ | 59.29 | 8.49 | 8.99 |

Example 32

83 Parts of t-butylhydroquinone, 19.8 parts of methyl 5,7,7-trimethyloct-4-enoate, and 5.0 parts of Fulmont ® 237 are reacted and worked up as described in Example 31. The product is distilled using a short-path rotary distillation at 0.13 mb and gives, after removing lower boilers, methyl 5-(4'-t-butyl-2',5'-dihydroxyphenol)-5,7,7-trimethyl-octanoate with the following percentage composition by weight.

|  | Carbon | Hydrogen |
|---|---|---|
| Found | 72.72 | 9.32 |
| Calculated for $C_{22}H_{36}O_4$ | 72.49 | 9.95 |

Example 33

The mother liquors from the preparation of 2',5'-bis-(5-methoxycarbonyl-2-methylpent-2-yl)-hydroquinone, in Example 1, are concentrated and then distilled. A fraction $b_{0.5}$ 160°–240° C. was collected and diluted with 40°–60° petroleum ether. From this solution there crystallises 2'-(5-methoxycarbonyl-2-methylpent-2-yl)-hydroquinone, m.p. 102°–4° C. with the following percentage composition by weight.

|  | Carbon | Hydrogen |
|---|---|---|
| Found | 66.65 | 7.99 |
| Calculated for $C_{14}H_{20}O_4$ | 66.45 | 8.45 |

Example 34

5.5 Parts of hydroquinone, 22.8 parts of 1,7-dimethoxycarbonyl-4-methylhept-3-ene and 1.0 parts of p-toluene sulphonic acid, are heated on a steam-bath for 3 days. After dilution with ether the reaction mixture is washed with sodium bicarbonate solution, water, evaporated and distilled to give dimethyl 5-methyl-5-(2',5'-dihydroxyphenyl)-azelate, $b_{0.1}$ 260°–9° C. with the following percentage composition by weight.

|  | Carbon | Hydrogen |
|---|---|---|
| Found | 64.34 | 7.92 |
| Calculated for $C_{18}H_{26}O_6$ | 63.89 | 7.74 |

EXAMPLE 35

41.4 Parts of 2-t-butylhydroquinone, 15.3 parts of diethyl 2-ethoxycarbonyl-5-methyl-hex-4-ene-2-phosphonate, and 5.0 parts of Fulmont ® 237 are stirred at 130° C. for 24 hours. The cooled reaction is diluted with ether, washed with 10% sodium hydroxide solution and then with water. After stripping off the ether, the residual oil is distilled and gives a fraction $b_{0.4}$ 89°–156° C. and a residue. This residue is chromatographed on a column established from 150 parts silica, and an initial solvent mixture comprising petroleum-ether (b.p. 40°–60° C.) and 5% ethylacetate. Column elution is carried out by increasing the percentage of ether, and ultimately with 50% ether present, diethyl 5-(4'-t-butyl-2',5'-dihydroxyphenyl)-2-ethoxycarbonyl-5-methyl-hexane-2-phosphonate is obtained as a viscous oil with the following percentage composition by weight.

|  | Carbon | Hydrogen | Phosphorus |
|---|---|---|---|
| Found | 61.16 | 8.52 | 6.61 |
| Calculated for $C_{24}H_{41}O_7P$ | 60.99 | 8.74 | 6.55 |

Example 36 2.2 Parts of hydroquinone, 8.5 parts of n-butyl citronellyl ether, and 0.5 parts of p-toluene sulphonic acid are heated on a steam-bath for 3 days. The work up follows Example 25 and, by short path distillation at 0.5 mb, there is obtained 2',5'-bis-(8-n-butoxy-2,6-dimethyl-oct-2-yl)-hydroquinone with m.p. 86°–9° C. and the following percentage composition by weight.

|  | Carbon | Hydrogen |
|---|---|---|
| Found | 76.43 | 11.88 |
| Calculated for $C_{34}H_{62}O_4$ | 76.35 | 11.68 |

Example 37

Similarly obtained by the procedure of Example 36, using 6.2 parts of citronellol in place of the n-butylcitronellyl ether is obtained 2',5'-bis-(2,6-dimethyl-8-hydroxyoct-2-yl)-hydroquinone as a viscous oil with the following percentage composition. by weight

|  | Carbon | Hydrogen |
|---|---|---|
| Found | 74.18 | 11.07 |
| Calculated for $C_{26}H_{46}O_4$ | 73.89 | 10.97 |

Example 38

By the procedure of Example 2, 4.8 parts of 2',5'-bis-(5-carboxy-2-methyl-pent-2-yl)-hydroquinone, 50 parts of tetrahydropyran-2-methanol, and 1.0 parts of p-toluene sulphonic acid are used to prepare 2,'5'-bis-(5-tetrahydropyran-4-yloxycarbonyl-2-methyl-pent-2-yl)-hydroquinone with m.p. 155°–8° C. and the following percentage composition by weight.

|  | Carbon | Hydrogen |
|---|---|---|
| Found | 68.62 | 9.05 |
| Calculated for $C_{32}H_{50}O_8$ | 68.30 | 8.96 |

Example 39

5.0 Parts of 2',5'-bis-(5-carboxy-2-methyl-pent-2-yl)-hydroquinone, 50 parts of commercial iso-octanol (mixed isomers, supplied by ICI Ltd.) and 1.0 parts of p-toluene sulphonic acid are reacted and worked up according to the procedure of Example 2. Short-path distillation at 0.5 mb using an oven temperature of 240° C. gave 2',5'-bis-(2-methyl-5-iso-octyloxycarbonyl-pent-2-yl)-hydroquinone as a viscous oil with the following percentage composition by weight.

|  | Carbon | Hydrogen |
|---|---|---|
| Found | 73.94 | 10.87 |
| Calculated for $C_{36}H_{62}O_6$ | 73.18 | 10.58 |

Example 40

1.1 Parts of hydroquinone, 4.5 parts of ethyl 2-ethoxycarbonyl-5-methyl-hex-4-enoate, and 0.5 parts of p-toluene sulphonic acid, are heated on a steam-bath for 3 days. The reaction mixture is then diluted with ether, washed with 10% sodium hydroxide solution, water and evaporated. Short-path rotary distillation at 0.7 mb removed lower-boilers at an oven temperature of 120° C. The residue is crystallised from petroleum-ether (b.p. 40°–60° C.) containing 5% ethyl acetate and gives 2',5'-bis-(5,5-diethoxycarbonyl-2-methyl-pent-2-yl)-hydroquinone with m.p. 157°–60° C. and the following percentage composition by weight.

|  | Carbon | Hydrogen |
|---|---|---|
| Found | 63.90 | 8.28 |
| Calculated for $C_{30}H_{45}O_{10}$ | 63.59 | 8.18 |

Examples of the Use of the new Hydroquinones of Formula I as stabilisers in colour photographic material

Use Example 1

0.05 mMol of the magenta coupler of the following formula

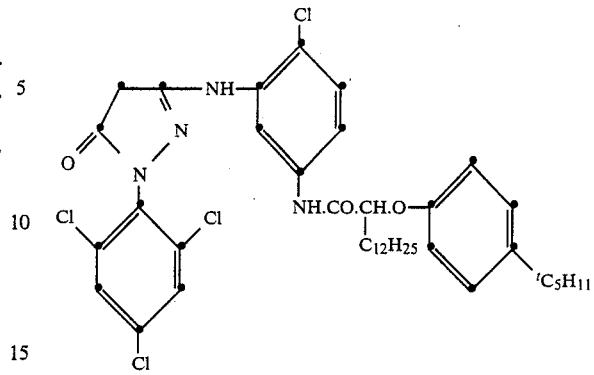

and 0.025 mMol of the compound of formula I are dissolved in 2.0 ml of tricresylphosphate/ethyl acetate (0.75 g./100 ml). 7.0 ml of a 6% gelatin solution, 1.0 ml of a 0.8% solution of the wetting agent of the formula

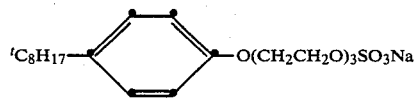

are put into water, then emulsified for 5 minutes by means of a 100-Watt ultra-sonic appliance. 2.5 ml of coupler-additive emulsion, freshly treated in the ultrasonic appliance, 2.0 ml of silver bromide emulsion with a content of 0.6% silver, 0.7 ml of a 1% aqueous solution of the curing agent with the following formula

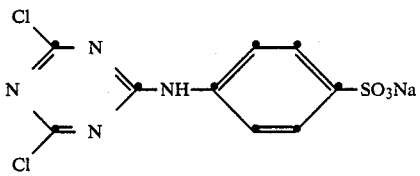

and 2.8 ml of water are mixed together, set to a pH value of 6.5, and at 40° C. poured onto a polyethylene paper measuring 14×18 cm. After the coating has hardened at 10° C., the poured-on mixture is dried at room-temperature.

Processing

The samples of the coated paper obtained are exposed to light of 500 Lux under a step-wedge for 6 seconds and then processed as follows at 32.8° C. (±0.3° C.):

| 1. | Developer bath | 3.5 minutes |
|---|---|---|
| 2. | Bleaching fixing bath | 1.5 minutes |
| 3. | Washing | 3.0 minutes |
| 4. | Drying | 1.0 minutes |

The developer bath has the following composition: 4-Amino-3-methyl-N-ethyl-N-[β-(methyl-sulphonamido)ethyl]-aniline

| 1½ $H_2SO_4.H_2O$ | 4.85 (g/liter) |
|---|---|
| Potassium bromide | 0.6 |
| Potassium carbonate | 32.0 |
| Lithium sulphate | 1.8 |
| Potassium sulphite | 2.0 |
| Hydroxylaminesulphite | 3.9 |

| -continued | |
|---|---|
| Ethyleneglycol | 21.3 |
| Benzyl alcohol | 15.1 |
| Water | to 1 liter |

The pH value is 10.1 The bleaching fixing bath used is a conventional bath, with e.g. the following composition:

| Ammoniumthiosulphate (80% solution) | 200 (g/liter) |
|---|---|
| Sodium sulphite (anhydrous) | 15 |
| Sodium carbonate (anhydrous) | 2.5 |
| Ethylenediamine tetra-acetic acid, sodium salt | 2 |
| Ethylenediamine tetra-acetic acid sodium-iron-(III)-salt | 50 |
| Water | to 1 liter |

After washing and drying, clear, sharp magenta wedges are obtained with absorption maximum at 537 nm and maximum densities of 2.28.

A step-wedge obtained in this way is exposed to light in the Atlas apparatus (2500-W lamp) with 42 kJ/cm$^2$ through an ultra-violet filter (Kodak filter 2C). For comparison, a step-wedge prepared analogously, which contains no compound according to the invention. In all cases the residual optical density (OD) was measured in % of the initial density (initial density 1). Table 1 contains the results.

TABLE 1

| Light Stabilising Effect of Compounds of Formula I | |
|---|---|
| Hydroquinone | % OD (with UV filter; 42 kJ/cm$^2$) |
| Without light stabiliser | 37 |
| Product of Example 9 | 80 |
| Product of Example 11 | 84 |
| Product of Example 12 | 87 |
| Product of Example 14 | 81 |
| Product of Example 15 | 85 |
| Product of Example 18 | 78 |
| Product of Example 25 | 76 |

Compared with the emulsion without stabiliser, emulsions containing the compounds of formula I are more stable to light.

Use Example 2

In an analogous series of experiments to those described in Use Example 1, further compounds of formula I were evaluated and the results are listed in Table 2.

TABLE 2

| Light Stabilising Effect of Compounds of Formula I | |
|---|---|
| Hydroquinone | % OD (with UV filter; 42 kJ/cm$^2$) |
| Without light stabiliser | 41 |
| Product of Example 19 | 85 |
| Product of Example 17 | 88 |
| Product of Example 29 | 87 |
| Product of Example 30 | 91 |
| Product of Example 32 | 78 |
| Product of Example 21 | 58 |
| Product of Example 24 | 55 |

Compared with the emulsion without stabiliser, emulsions containing compounds of formula I are more stable to light.

Use Example 3

Emulsion prepared according to Example 1, but containing 0.05 mMol of the Magenta coupler of the following formula:

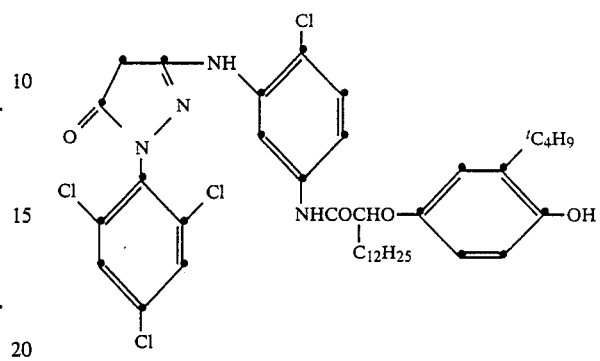

instead of the magenta coupler of the following formula:

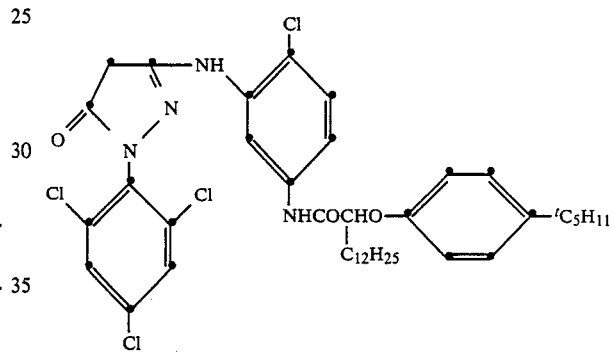

containing 0.025 mMol of Example 9 was processed analogously and exposed to 42 kJ/cm$^2$ in the Atlas apparatus. The increase in density measured at a wavelength of 436 (yellowing) was measured. The following values were obtained.

TABLE 3

| Light Stabilising Effect of Product of Example 9 | |
|---|---|
| Hydroquinone | Increase 100 D$_{436}$ after 42 kJ/cm$^2$ in the Atlas apparatus |
| Without light stabiliser | 10 |
| Product of Example 9 | −1 |

Compared with the emulsion without stabiliser, emulsions containing the product of Example 9 show no increase in density 436.

Example 41

5.0 Parts of 2',5'-bis-(5-carboxy-2-methyl-pent-2-yl)-hydroquinone, 50 parts of an amyl/isobutyl alcohol mixture (supplied by Hoechst AG) and 0.5 parts of p-toluene sulphonic acid were reacted and worked up according to the procedure of Example 2. The ethereal solution after being concentrated was then diluted with 60°-80° petroleum-ether to yield a mixture of the amyl and isobutyl esters of the starting material acid with m.p. 106°-20° C. and the following percentage composition by weight.

| | Carbon | Hydrogen |
|---|---|---|
| Found | 70.82 | 9.82 |
| Calculated for $C_{29}H_{48}O_6$ | 70.70 | 9.82 |

Example 42

By the procedure of Example 39, 50 parts of Epal 108 (n-decanol/octanol mixture supplied by the Ethyl Corporation) was used to esterify 5.0 parts of 2′,5′-bis-(5-carboxy-2-methyl-pent-2-yl)-hydroxquinone. Short-path distillation gave the ester product as a viscous oil with the following percentage composition by weight.

| | Carbon | Hydrogen |
|---|---|---|
| Found | 74.49 | 11.00 |
| Calculated for $C_{38}H_{66}O_6$ | 73.74 | 10.75 |

Use Example 4

In an analogous series of experiments to those described in Use Example 1, further compounds of formula 1 were evaluated and the results are listed in Table 4.

TABLE 4

| Hydroquinone | % OD (with UV filter; 42 kJ/cm²) |
|---|---|
| Without light stabiliser | 45 |
| Product of Example 16 | 87 |
| Product of Example 27 | 80 |
| Product of Example 41 | 90 |
| Product of Example 42 | 90 |

Use Example 5

In an analogous series of experiments to those described in Use Example 1, further compounds of formula 1 were evaluated and the results are listed in Table 5.

TABLE 5

| Hydroquinone | % OD (with UV filter; 21 kJ/cm²) |
|---|---|
| Without light stabiliser | 84 |
| Product of Example 35 | 94 |
| Product of Example 36 | 97 |
| Product of Example 37 | 93 |
| Product of Example 38 | 96 |
| Product of Example 39 | 98 |
| Product of Example 40 | 96 |
| Product of Example 41 | 98 |

I claim:

1. A hydroquinone compound of the formula:

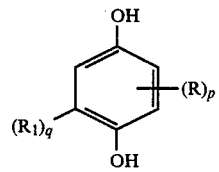

wherein p is 1 or 2 and q is 0 or 1, provided that p+q is 1 or 2;

R is a group of the formula

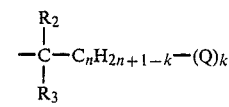

wherein Q is a number selected from the groups:
(i) —OX wherein X is $R_5$ or $COR_7$ wherein $R_5$ is hydrogen or a straight or branched chain alkyl group having from 1 to 20 carbon atoms,
$R_7$ is hydrogen or a straight or branched chain alkyl group having from 1 to 20 carbon atoms, a straight or branched chain alkenyl group having from 3 to 20 carbon atoms, a cycloalkyl group having from 3 to 12 carbon atoms, an aralkyl group having from 7 to 13 carbon atoms or an unsubstituted or mono- or di-$C_1$-$C_4$-alkyl substituted aryl group having from 6 to 10 carbon atoms, and
(ii) —$PO(OR_{10})((O)_xR_{11})$ wherein X is 1, $R_{10}$ and $R_{11}$ are the same or different and each is hydrogen or a straight or branched chain alkyl group having from 1 to 20 carbon atoms, n is an integer from 2 to 20:

k is 1 or 2;

$R_2$ and $R_3$ are the same or different and each is a straight or branched chain alkyl group having from 1 to 5 carbon atoms; and $R_1$ is a straight or branched chain alkyl group having from 1 to 8 carbon atoms, or a group of formula II as hereinbefore defined and, when $R_1$ is a group of formula II, then $R_1$ and R may be the same or different; or a salt thereof with an organic or inorganic acid or base.

2. A compound according to claim 1 wherein p, q, R, Q, $R_1$, $R_2$, $R_3$, $R_5$, $R_7$, p, k and n are as defined in claim 9; and $R_{10}$ and $R_{11}$, when x is 1, are the same or different and each is hydrogen or a straight or branched chain alkyl group having from 1 to 20 carbon atoms; or a salt thereof.

3. A compound according to claim 1 wherein the groups R and $R_1$ are bonded in the 2- or 5-positions, respectively; or a salt thereof.

4. A compound according to claim 1 of the formula:

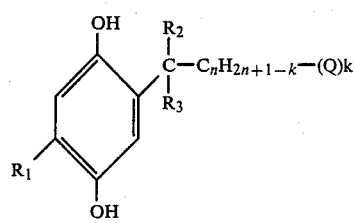

wherein $R_2$, $R_3$, Q, n and k are as defined in claim 1; and $R_1$ is a group of formula II as defined in claim 1, or is a group of formula:

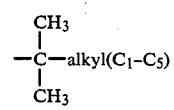

or a salt thereof.

5. A compound of formula III according to claim 4 wherein
$R_1$ is as defined in claim 4;

Q is —$OR_5$ wherein $R_5$ is hydrogen or a straight or branched chain alkyl group having from 1 to 20 carbon atoms; and $R_2$ and $R_3$, independently, are methyl, ethyl, n-propyl, isopropyl or neopentyl; or a salt thereof.

6. A compound of formula III according to claim 5 wherein k is 1;

$R_1$ is a group of the formula

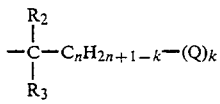     II or of the formula

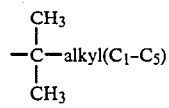     IV

Q is —$OR_5$;

n is an integer from 2 to 10, and $R_2$ and $R_3$, independently, are methyl, ethyl or neopentyl; or a salt thereof.

7. A compound of formula III according to claim 6 wherein k is 1;

$R_1$ is a group of the formula

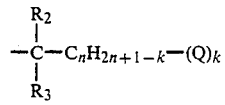     II or of the formula

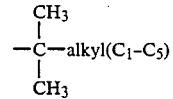     IV

Q is —$OR_5$ wherein $R_5$ is hydrogen or $C_1$-$C_{15}$ alkyl;

n is an integer from 2 to 10; and $R_2$ and $R_3$, independently, are methyl, ethyl or neopentyl; or a salt thereof.

8. The compound 2,5-bis-(8-n-butoxy-2,6-dimethyl)-oct-2-yl)-hydroquinone.

* * * * *